United States Patent [19]
Umezawa et al.

[11] 3,940,382
[45] Feb. 24, 1976

[54] 1,2'-DI-N-SUBSTITUTED KANAMYCIN B COMPOUNDS

[75] Inventors: Hamao Umezawa; Kenji Maeda, both of Tokyo; Shinichi Kondo, Yokohama; Sumio Umezawa, Tokyo, all of Japan

[73] Assignee: Zaidan Hojin Biseibutsu Kagaku Kenkyu Kai, Tokyo, Japan

[22] Filed: Aug. 22, 1974

[21] Appl. No.: 499,601

[30] Foreign Application Priority Data
Aug. 29, 1973  Japan.................................. 48-96177

[52] U.S. Cl........ 260/210 K; 260/210 AB; 424/180
[51] Int. Cl.$^2$........................................ C07H 15/22
[58] Field of Search................... 260/210 AB, 210 K

[56] References Cited
UNITED STATES PATENTS

| | | | |
|---|---|---|---|
| 3,296,246 | 1/1967 | Ores et al...................... | 260/210 AB |
| 3,478,015 | 11/1969 | Onishi.............................. | 260/211 R |
| 3,652,536 | 3/1972 | Sebek et al.................... | 260/210 AB |
| 3,781,268 | 12/1973 | Kawaguchi et al........... | 260/210 AB |

*Primary Examiner*—Johnnie R. Brown
*Attorney, Agent, or Firm*—James C. Haight

[57] ABSTRACT

New antibacterial agents, 1,2'-di-N-(α-hydroxyaminoacyl)-kanamycin B and 1,2'-di-N-(α-hydroxyaminoacyl)-3',4'-dideoxy kanamycin B are described together with methods for their preparation and use.

5 Claims, No Drawings

1,2'-DI-N-SUBSTITUTED KANAMYCIN B COMPOUNDS

This invention relates to new kanamycin B derivatives, that is, a 1,2'-di-N-(α-hydroxy-aminoacyl)-kanamycin B or -3',4'-dideoxykanamycin B which is useful for the treatment of various bacterial infections. More particularly, this invention relates to a new kanamycin B derivative which is selected from 1,2'-di-N-(4-amino-2-hydroxybutyryl)-kanamycin B; 1,2'-di-N-(4-amino-2-hydroxybutyryl)-3',4'-dideoxykanamycin B; 1,2'-di-N-isoserylkanamycin B and 1,2'-di-N-isoseryl-3',4'-dideoxykanamycin B. Moreover, this invention relates to a process for the production of these 1,2'-di-N-(α-hydroxy-aminoacyl) derivatives of kanamycin B and 3',4'-dideoxykanamycin B.

Kanamycins are well known aminoglycosidic antibiotics. Kanamycin A (usually merely called kanamycin) and kanamycin B have widely been used as valuable chemotherapeutic agents, but many drug-resistant strains which are resistant to these kanamycins have occurred in recent years. In these circumstances, the mechanism of resistance of the drug-resistant bacteria to the known aminoglycosidic antibiotics has been studied. For instance, one of the present inventors, H. Umezawa et al have found that some R-factor carrying strains of gram-negative bacteria, *Staphylococcus aureus* and *Pseudomonas aeruginosa* isolated from patients, are resistant to the action of kanamycins and that these kanamycin-resistant strains have as a mechanism of resistance the production of enzymes capable of phosphorylating the 3'-hydroxyl group of kanamycins and inactivating the kanamycins with aid of these phosphorylating enzymes, (see *Science* Vol. 157, page 1559 (1967).

On the basis of this finding, H. Umezawa et al prepared semi-synthetically 3'-deoxykanamycin and 3',4'-dideoxykanamycin B in which the 3'-hydroxyl group of the kanamycin molecule is removed therefrom, as described in the *Journal of Antibiotics* Ser. A, Vol. 21, pages 274–275 (1968) and Vol. 24, pages 485–487 (1971). 3'-deoxykanamycin and 3',4'-dideoxykanamycin B are actually effective against the above-mentioned kanamycin-resistant strains. While, it has been found that 3'-deoxykanamycin and 3',4'-dideoxykanamycin B are practically inactive against other kanamycin-resistant strains such as *Escherichia coli* JR66/W677 which has been isolated from patients. H. Umezawa et al. have found that the latter kind of kanamycin-resistant strains have as a mechanism of resistance the production of an enzyme capable of adenylylating the 2''-hydroxyl group of the kanamycin or 3',4'-dideoxykanamycin B molecule with ATP (adenosine triphosphate) and thus inactivate kanamycin and 3',4'-dideoxykanamycin B through the action of this adenylylating enzyme; see the *Journal of Antibiotics* Vol. 24, pages 911–913 (1971).

On the other hand, it is known that butirosin B, which is an aminoglycosidic antibiotic produced by a microorganism Bacillus species, is active against some kanamycin-resistant bacteria as well as against some ribostamycin-resistant bacteria. Butirosin B has been identified as 1-N-[(S)-α-hydroxy-γ-amino-n-butyryl]-ribostamycin; see *Tetrahedron Letters* Vol. 28, page 2125 and pages 2617–2630 (1971) and German Offenlegungsschrift No. 1914527. From comparison of the antibacterial activity of ribostamycin with that of butirosin B, it has been appreciated that the (S)-α-hydroxy-γ-amino-butyryl substituent at the 1-amino group of the butirosin B molecule has an important role in enabling the substituted ribostamycin to be active against both ribostamycin-resistant and -sensitive strains, and that the presence of the (S)-α-hydroxy-γ-amino-butyryl substituent at the 1-amino group of the butirosin B molecule results in a steric hindrance of the butirosin B molecule owing to which the butirosin B can be prevented from being inactivated by attack of the various inactivating enzymes which are produced by the kanamycin-resistant strains or ribostamycin-resistant strains.

On the basis of these findings, H. Umezawa et al. have synthetized new compounds, that is, 3'-deoxykanamycin B; 3'-deoxy-6'-N-methylkanamycin B; 3',4'-dideoxykanamycin B; 3'-deoxyneamine; 3',4'-dideoxyneamine; 3'-deoxyribostamycin; 3',4'-dideoxyribostamycin; and 1-N-[(S)-4-amino-2-hydroxybutyryl] derivatives of kanamycin B and 3',4'-dideoxykanamycin B and have found that these new compounds exhibit improved antibacterial activity against the drug-resistant bacteria; see copending U.S. patent application Ser. No. 402,085 filed Oct. 1, 1973; British patent application No. 46,397/73; German patent application No. P 23 50169.1 and French patent application No. 73 36291, as well as the *Journal of Antibiotics* Vol. 26, pages 304–309 (May 1973). Furthermore, H. Umezawa et al have synthetized 1-N-isoserylkanamycin, 1N-isoserylkanamycin B and 1-N-isoseryl-3',4'-dideoxykanamycin B which are effective against the gram-negative and gram-positive bacteria sensitive to the kanamycins and also against drug-resistant bacteria (see co-pending U.S. patent application Ser. No. No. 466,053 filed May 1, 1974; British patent application No. 18938/74; Germany patent application No. P 24 23 591.4 and French patent application No. 74 17,382).

Accordingly, we have made our further research to seek new and useful derivatives of kanamycin B and 3',4'-dideoxykanamycin B which are effective not only against the gram-negative and gram-positive bacteria but also against the drug-resistant bacteria. As a result, we have now found that acylation of the 1- and 2'-amino group of kanamycin B and 3',4'-dideoxykanamycin B with an α-hydroxy-amino acid which is 4-amino-2-hydroxybutyric acid or isoserine, either in the racemic form or in the form of the L-isomer or the D-isomer, gives new and useful kanamycin B derivatives which exhibit a useful antibacterial activity against gram-negative and gram-positive bacteria as well as against, kanamycin-resistant bacteria.

An object of this invention is, therefore, to provide as new and useful kanamycin B derivatives 1,2'-N-(4-amino-2-hydroxybutyryl)-kanamycin B; 1,2'-di-N-(4-amino-2-hydroxybutyryl)-3',4'-dideoxykanamycin B; 1,2'-di-N-isoserylkanamycin B and 1,2-di-N-isoseryl-3',4'-dideoxykanamycin B which show useful antibacterial activity against kanamycin-sensitive and resistant bacteria. The other object of this invention is to provide a process for the production of these new kanamycin B derivatives which is carried out in a facile way and in a favorable yield of the desired product. Another objects of this invention will be clear from the following descriptions.

We have now succeeded in synthesizing the 1,2'-di-N-(4-amino-2-hydroxybutyryl) or 1,2'-di-N-isoseryl derivatives of kanamycin B and 3',4'-dideoxykanamycin B by protecting partially and wholly the amino groups other than the 1- and 2'-amino groups of kanamycin B or 3',4'-dideoxykanamycin B with a known amino-protecting group in a known manner, then reacting the resulting amino-protected derivative of kanamycin B or 3',4'-dideoxykanamycin B with an α-hydroxy-amino acid which is selected from 4-amino-2-hydroxybutyric acid and isoserine to acylate both the 1- and 2'-amino groups of the kanamycin B compound, removing the amino-protecting groups from the resultant acylation products and then isolating the desired product in a chromatographic manner. It has further been found that the new kanamycin B derivatives so prepared exhibit a usefully high anti-bacterial activity against the gram-negative and gram-positive bacteria sensitive to kanomycins and 3',4'-dideoxykanamycin B, as well as against some drug-resistant bacteria.

According to a first aspect of this invention, there is provided a new compound selected from 1,2'-di-N-(4-amino-2-hydroxybutyryl)-kanamycin B, 1,2'-di-N-(4-amino-2-hydroxybutyryl)-3',4'-dideoxykanamycin B 1,2'-di-N-isoserylkanamycin B and 1,2'-di-N-isoseryl-3',4'-dideoxykanamycin B, which are generically represented by a 1,2'-di-N-(α-hydroxy-aminoacyl)-kanamycin B or -3',4'-dideoxykanamycin B of the following general formula:

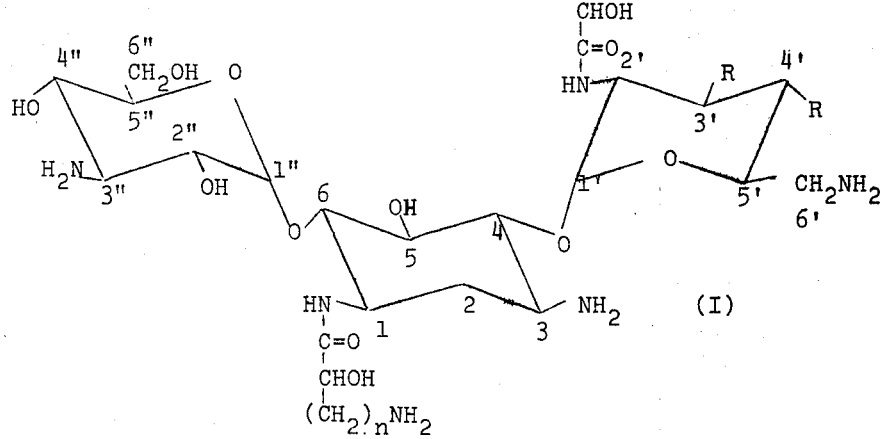

wherein each R is a hydroxyl group or a hydrogen atom and n is an integer of 1 or 2, and the pharmaceutically acceptable acid-addition salt thereof. The α-hydroxy-aminoacyl moiety, that is the 4-amino-2-hydroxybutyryl or isoseryl moiety, in the molecule of the new compound of the above formula (I) may be either in the DL-form or in the L-form (namely, the S-form) or in the D-form (namely, the R-form).

Examples of pharmaceutically acceptable acid-addition salts of the compound of the above-mentioned general formula (I) according to this invention include the hydrochloride, sulfate, phosphate, carbonate, acetate, maleate, fumarate, succinate, tartrate, oxalate, citrate, methanesulfonate, ethanesulfonate and the like.

The compounds according to this invention have the following physical, chemical and biological properties: Thus, 1,2'-di-N-[(S)-4-amino-2-hydroxybutyryl]-kanamycin B is a substrate in the form of a colorless crystalline powder with a decomposition point of 117°–180°C., $[\alpha]_D^{26} = +65°$ (c 1.25, water). Its elemental analysis is coincident with the theoretical values of $C_{26}H_{51}N_7O_{14} \cdot 2H_2CO_3$ (C 41.53%, H 6.85%, N 12.11%). This substance gives a single spot positive to the ninhydrin reaction at Rf 0.08 in a thin layer chromatography of silica gel (available under a trade name "ART 5721", a product of Merck Co., Germany) using a solvent system of butanol-ethanol-chloroform-17% aqueous ammonia (4:5:2:8 by volume) and at Rf 0.04 on a thin layer chromatography of the same silica gel using a solvent system of methanol-chloroform-28% aqueous ammonia-water (4:1:2:1 by volume) as the development solvent, respectively.

1,2-di-N-[(S)-4-amino-2-hydroxybutyryl]-3',4'-dideoxykanamycin B is a substance in the form of a colorless crystalline powder with a decomposition point of 168°–170°C., $[\alpha]_D^{24} = +78°$ (c 1.14, H₂O). Its elemental analysis is coincident with the theoretical values of $C_{26}H_{51}N_7O_{12} \cdot 2H_2CO_3$ (C 43.24%, H 7.13%, N 12.61%). This substance gives a single spot positive to the ninhydrin reaction at Rf 0.09 in the above-mentioned thin layer chromatography of silica gel using a solvent system of butanol-ethanol-chloroform-17% aqueous ammonia (4:5:2:5 by volume) and at Rf 0.15 on the same thin layer chromatography of silica gel using a solvent system of methanol-chloroform-28% aqueous ammonia-water (4:1:2:1 by volume), respectively.

1,2'-di-N-DL-isoseryl-3',4'-dideoxykanamycin B is a substance in the form of a colorless crystalline powder with a decomposition point of 175°–178°C, $[\alpha]_D^{27} = +96°$ (c 1.40, H₂O). Its elemental analysis is coincident with the theoretical values of $C_{24}H_{47}N_7O_{12} \cdot 2H_2CO_3$ (C 41.65%, H 6.86%, N 13.08%). This substance gives a single spot positive to the ninhydrin reaction at Rf 0.08 in the above-mentioned thin layer chromatography of silica gel using a solvent system of butanol-ethanol-chloroform-17% aqueous ammonia (4:5:2:5 by volume) and at Rf 0.26 on the same thin layer chromatography using methanol-chloroform-28% aqueous ammonia-water (4:1:2:1 by volume), respectively.

1,2'-di-N-DL-isoseryl-kanamycin B is a substance in the form of a colorless crystalline powder with a decomposition of 180°–185°C, $[\alpha]_D^{27} = +85°$ (c 1.0, H₂O). Its elemental analysis is coincident with the theoretical values of $C_{24}H_{47}N_7O_{14} \cdot 2H_2CO_3$ (C 39.95%, H 6.58%, N 12.54%). This substance gives a single spot positive to the ninhydrin reaction at Rf 0.06 in the above-mentioned thin layer chromatography of silica gel using a solvent system of butanol-ethanol-chloroform-17% aqueous ammonia (4:5:2:5 by volume) as the development solvent.

mycin B (abbreviated as DKB) were also determined in the same manner as mentioned above.

The antibacterial spectra of these substances are shown in Table 1 below.

Table 1

| Test Organisms | Minimum Inhibitory Concentrations (mcg/ml) | | | | | |
|---|---|---|---|---|---|---|
| | 1,2'-AHB-KMB | 1,2'-AHB-DKB | 1,2'-IS-DKB | 1,2'-IS-KMB | KMB | DKB |
| *Staphylococcus aureus* Smith | 0.39 | 0.20 | — | — | 0.39 | <0.20 |
| *Staphylococcus aureus* FDA 209P | 6.25 | 0.78 | 1.56 | 3.13 | <0.20 | <0.20 |
| *Staphylococcus aureus* Terejima | <0.20 | <0.20 | — | — | <0.20 | <0.20 |
| *Sarcina lutea* PCI 1001 | 6.25 | 1.56 | — | — | 1.56 | 6.25 |
| *Bacillus anthracis* | 0.39 | <0.20 | — | — | <0.20 | <0.20 |
| *Bacillus subtilis* PCI 219 | <0.20 | <0.20 | — | — | <0.20 | <0.20 |
| *Bacillus subtilis* NRRL B-558 | 0.78 | 0.20 | — | — | <0.20 | <0.20 |
| *Bacillus cereus* ATCC 10702 | 12.5 | 1.56 | — | — | 0.78 | 0.78 |
| *Corynebacterium bovis* 1810 | 3.13 | 0.78 | — | — | 1.56 | 3.13 |
| *Mycobacterium smegmatis* ATCC 607 | 0.78 | 0.20 | 1.56 | 1.56 | 0.78 | 0.39 |
| *Shigella dysenteriae* JS 11910 | 12.5 | 6.25 | — | — | 3.13 | 1.56 |
| *Shigella flexneri* 4b JS 11811 | 12.5 | 6.25 | — | — | 3.13 | 1.56 |
| *Shigella sonnei* JS 11746 | 6.25 | 6.25 | — | — | 1.56 | 0.78 |
| *Salmonella typhosa* T-63 | 3.13 | 0.78 | — | — | 0.20 | <0.20 |
| *Salmonella enteritidis* 1891 | 3.13 | 1.56 | — | — | 1.56 | 1.56 |
| *Proteus vulgaris* OX 19 | 3.13 | 0.78 | — | — | 0.78 | <0.20 |
| *Klebsiella pneumoniae* PCI 602 | 3.13 | 0.78 | 3.13 | 3.13 | 0.78 | 0.39 |
| *Klebsiella pneumoniae* 22 3038 | 3.13 | 1.56 | 12.5 | 12.5 | >100 | 100 |
| *Escherichia coli* NIHJ | 6.25 | 3.13 | 6.25 | 6.25 | 0.78 | 0.39 |
| *Escherichia coli* K-12 | 3.13 | 1.56 | 6.25 | 6.25 | 0.78 | 0.78 |
| *Escherichia coli* K-12 ML 1629 | 3.13 | 3.13 | 6.25 | 6.25 | >100 | 0.78 |
| *Escherichia coli* K-12 ML 1630 | 3.13 | 3.13 | 6.25 | 6.25 | >100 | 0.78 |
| *Escherichia coli* K-12 ML 1410 | 3.13 | 3.13 | 6.25 | 6.25 | 0.78 | 1.56 |
| *Escherichia coli* K-12 ML 1410 R81 | 6.25 | 1.56 | 6.25 | 6.25 | >100 | 1.56 |
| *Escherichia coli* LA290 R55 | 3.13 | 0.78 | 6.25 | 6.25 | 12.5 | 50 |
| *Escherichia coli* LA290 R56 | 1.56 | 0.78 | 6.25 | 6.25 | 3.13 | 12.5 |
| *Escherichia coli* LA290 R64 | 1.56 | 0.78 | 6.25 | 6.25 | 3.13 | 6.25 |
| *Escherichia coli* W677 | 1.56 | 1.56 | 3.13 | 3.13 | 0.39 | 0.20 |
| *Escherichia coli* JR66/W677 | 6.25 | 6.25 | 12.5 | 25 | >100 | 50 |
| *Pseudomonas aeruginosa* A3 | 12.5 | 25 | 6.25 | 12.5 | 50 | 1.56 |
| *Pseudomonas aeruginosa* No.12 | 25 | 6.25 | 25 | 25 | 12.5 | 0.78 |
| *Pseudomonas aeruginosa* TI-13 | 25 | 12.5 | 12.5 | 12.5 | 100 | 1.56 |
| *Pseudomonas aeruginosa* GN315 | >100 | 100 | >100 | >100 | >100 | >100 |
| *Pseudomonas aeruginosa* 99 | 50 | 50 | 50 | 50 | >100 | 3.13 |

The ultra-violet absorption spectrum of the above substances in aqueous solution show only the end absorption and the infra-red absorption spectra in a potassium bromide pellet reveal the presence of the amido-linkage in the molecule thereof. From the nuclear magnetic resonance spectra, it is shown that each substance is a compound in the molecule of which kanamycin B or 3',4'-dideoxykanamycin B has been condensed with the α-hydroxy-amino acid in a molar ratio of 1:2.

Moreover, the above specified four substances exhibit a high antibacterial activity not only against various gram-negative and grame-positive bacteria which are sensitive to kanamycins, but also against the drug-resistant strains of *Escherichia coli* and *Pseudomonas aeruginosa*, as shown in Table 1 below. These substances are of low toxicity to animals and men as shown by the fact that they exhibit an $LD_{50}$ of more than 100 mg/kg upon intravenous injection in mice.

The minimum inhibitory concentrations (mcg/ml) of 1,2'-di-N-[(S)-4-amino-2-hydroxybutyryl]-kanamycin B (abbreviated as 1,2'-AHB-KMB), 1,2'-di-N-[(S)-4-amino-2-hydroxybutyryl]-3',4'-dideoxykanamycin B (abbreviated as 1,2'-AHB-DKB), 1,2'-di-N-DL-isoseryl-3',4'-dideoxykanamycin B (abbreviated as 1,2'-IS-DKB) and 1,2'-di-N-DL-isoseryl-kanamycin B (abbreviated as 1,2'-IS-KMB) against various microorganisms were determined according to serial dilution method using nutrient agar medium at 37°C, the estimation being effected after 18 hours incubation. For comparison, the minimum inhibitory concentrations of kanamycin B (abbreviated as KMB) and 3',4'-dideoxykana- The new compounds of this invention, namely 1,2'-di-N-(α-hydroxy-aminoacyl)-kanamycin B or -3',4'-dideoxykanamycin B of the general formula (I) are of low toxicity to animals and men, as show an $LD_{50}$ value of more than 100 mg/kg upon intravenous injection of the compound in mice. In addition, the new compounds of this invention exhibit a high antibacterial activity against various gram-positive and gram-negative bacteria, including the kanamycin-resistant strains, so that the new compounds of this invention may be useful in treatment of infections of gram-positive and gram-negative bacteria. The compounds of this invention may be administered orally, intraperitoneally, intravenously, subcutaneously or intamuscularly using any pharmaceutical form known to the art for such administration and in a similar manner to kanamycins. For instance, the compounds of the formula (I) of this invention may be administered orally using any pharmaceutical form known to the art for such oral administration. Examples of pharmaceutical forms for oral administration are powders, capsules, tablets, syrup, and the like. A suitable dose of the compound for the effective treatment of bacterial infections is in a range of 0.25–2 g per person a day when it is given orally. It is preferred that said dose should be orally administered in three to four aliquots per day. The compounds of this invention may also be administered by intramuscular injection at a dosage of 100–500 mg per person two to four times per day. Moreover, the new compounds of the invention may be formulated into an ointment for external application which contains a compound of this invention at a concentration of 0.5–5% by weight in mixture with a known ointment base such as polyethylene glycol.

The compounds of the formula (I) according to this invention may principally be produced from kanamycin B and 3′,4′-dideoxykanamycin B, respectively, which are represented by the following general formula:

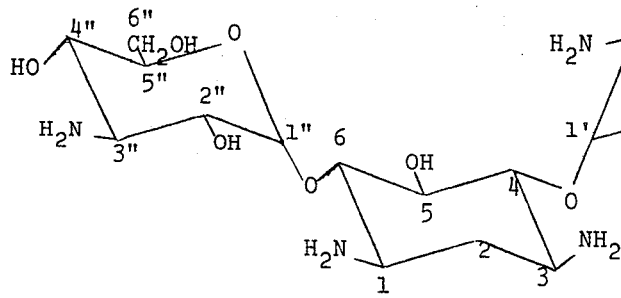
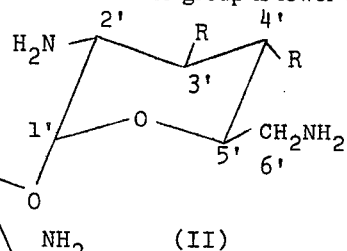

(II)

wherein each R is a hydroxyl group or a hydrogen atom, by acylating the starting compound kanamycin B or 3′,4′-dideoxykanamycin B of the general formula (II) selectively at the 1- and 2′-amino groups thereof with an α-hydroxy-amino acid of the general formula:

$$H_2N-(CH_2)_n-CH(OH)-COOH \quad (III)$$

wherein $n$ is a whole number of 1 or 2, in a manner known for the prior art of acylating the amino group. The starting materials kanamycin B and 3′,4′-dideoxykanamycin B contain five amino groups all per molecule thereof. In order to achieve the production of 1,2′-di-N-(α-hydroxy-aminoacyl)-kanamycin B or -3′,4′-dideoxykanamycin B of the general formula (I) according to this invention, it is required that only the 1-amino and 2′-amino groups of the starting kanamycin B or 3′,4′-dideoxykanamycin B of the general formula (II) should selectively be acylated by the α-hydroxy-amino acid of the general formula (III) without involving the acylation of the other amino groups. It will be obvious that the desired new compound of the formula (I) would be obtained in a best yield if the α-hydroxy-amino acid reactant of the formula (III) is reacted with such an amino-protected derivative of the starting compound of the formula (II) in which all the amino groups other than the 1- and 2′-amino groups (namely, all the 6′-, 3- and 3″-amino groups of kanamycin B and 3′,4′-dideoxykanamycin B) have been blocked by a known amino-protecting group while the 1- and 2′-amino groups remain free. The preparation of such amino-protected derivative of the starting compound of the formula (II) is possible, but needs a very complicated method comprising a number of reaction steps for preparation. In this situation, it is rather preferred to prepare an amino-protected derivative of the starting compound of the formula (II) in which only the primary 6′-amino group of the starting compound (II) has been blocked by the amino-protecting group with the 1- and 2′-amino groups remaining in the free state, because the preparation of such amino-protected derivatives is relatively easier and simpler owing to the fact that the 6′-amino group is the most reactive of the amino groups of the starting compound (II) and is hence capable of being protected preferentially with the amino-protecting group with keeping the other amino groups unblocked. The reactivity of the 2′-amino group is lower than that of the 6′-amino group but higher than that of the other amino groups.

When the so prepared amino-protected derivative of the compounds (II) in which the 6′-amino group has been blocked is reacted with the α-hydroxy-amino acid of the formula (III) of which the amino group may preferably be blocked with an amino-protecting group, there may be formed a mixture of different acylation products comprising the desired 1,2′-di-N-acylated product in which only the 1- and 2′-amino groups have been acylated with the α-hydroxy-amino acid (III), as well as such undesired mono- or poly-N-acylated products of which one or more of the amino groups other than the 1- and 2′-amino groups has been acylated with the α-hydroxy-amino acid (III), respectively. When these mixed N-acylated products so formed are treated so as to remove the amino-protecting groups therefrom, there are produced such mixed N-acylated derivatives of the starting compound (II) comprising the desired 1,2′-di-N-acylated product of the formula (I) as well as the undesired mono- or poly-N-acylated products from which the amino-protecting groups have already been liberated. The desired 1,2′-di-N-acylated product (I) may be isolated from said mixed N-acylated derivatives in a chromatographic manner separately from the other undesired N-acylated products.

According to a second aspect of this invention, therefore, there is provided a process for the production of the compounds of the aforesaid general formula (I), which comprises acylating a compound of the general formula:

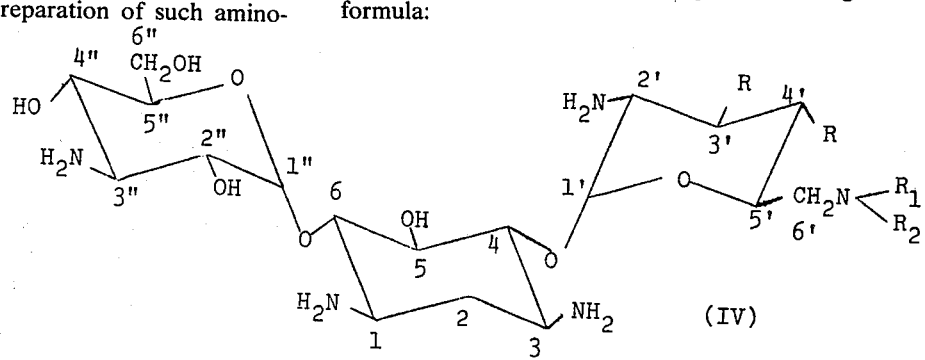

(IV)

wherein each R is a hydroxyl group or a hydrogen atom and $R_1$ is a known mono-valent amino-protecting group and $R_2$ is a hydrogen atom, or $R_1$ and $R_2$ taken together form a known divalent amino-protecting group, with an α-hydroxy-amino acid of the formula:

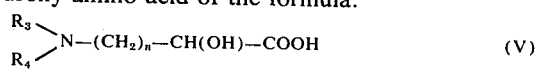

(V)

wherein $R_3$ is a known mono-valent amino-protecting group and $R_4$ is a hydrogen atom, or $R_3$ and $R_4$ taken together form a known divalent amino-protecting group, and n is an integer of 1 or 2, to produce the mixed N-acylated products containing the desired intermediate acylation product of the formula:

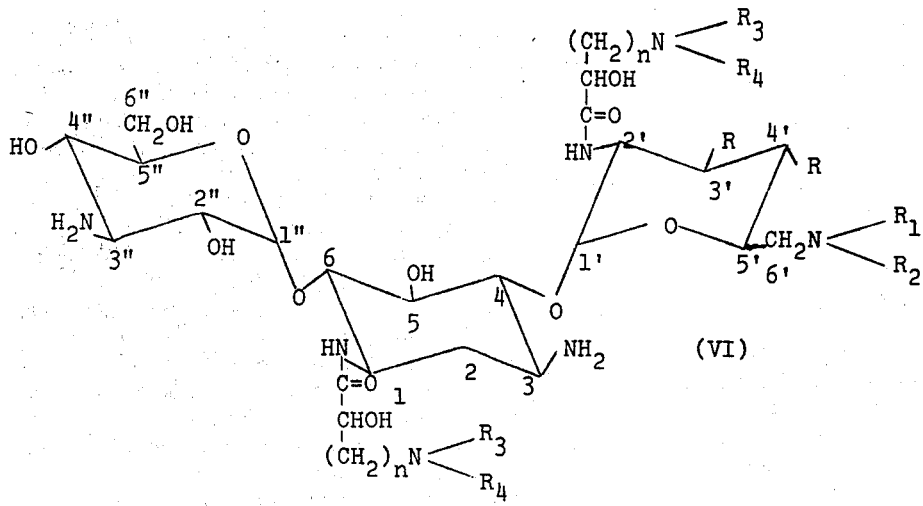

wherein R, $R_1$, $R_2$, $R_3$, $R_4$ and n are each as defined above, removing the amino-protecting groups from said mixed N-acylated products, and then isolating the desired compound of the formula (I) out of the mixed N-acylated products which have been freed from the amino-protecting groups.

To prepare the compound having the amino group protected according to the above formula (IV) which is employed as the starting material in the process of this invention, kanamycin B or 3',4'-dideoxykanamycin B, that is, a compound of the above formula (II), is reacted with a reagent which is known and is commonly used in the conventional synthesis of peptides to introduce a known amino-protecting group. Accordingly, the above-mentioned known amino-protecting group available in this invention may be any of the amino-protecting groups which are commonly known and used in the conventional synthesis of peptides, as long as it is capable of being removed readily from the acylation products of the acylation step of the present process by treating the acylation products in a known manner for the removal of the amino-protecting group without substantially affecting the amide linkages of the acylation products which have already been formed between the α-hydroxy-aminoacyl radical and the kanamycin B moiety of the acylation products.

As suitable examples of the known amino-protecting groups for the $R_1$, $R_2$, $R_3$ and $R_4$ which are available in this invention, there may be mentioned an alkyloxycarbonyl group of 2–6 carbon atoms such as ethoxycarbonyl, t-butoxycarbonyl and t-amyloxycarbonyl; a cycloalkyloxycarbonyl group of 4–7 carbon atoms such as cyclopentyloxycarbonyl and cyclohexyloxycarbonyl; an aralkyloxycarbonyl group such as benzyloxycarbonyl and p-nitrobenzyloxycarbonyl; an aryloxycarbonyl group such as phenoxycarbonyl and furfuryloxycarbonyl; and an acyl group such as o-nitrophenoxyacetyl and the like. When a pair of the groups $R_1$ and $R_2$ or a pair of the groups $R_3$ and $R_4$ taken together forms a known divalent amino-protecting group, this divalent amino-protecting group may be a phthaloyl group or a salicyclidene group and generally an alkylidene or arylidene group of the formula =$CHR_5$ in which $R_5$ is an alkyl group of 1–6 carbon atoms such as methyl, ethyl, propyl, isopropyl, butyl or pentyl, or an aryl group such as phenyl, tolyl, p-methoxyphenyl or o-hydroxylphenyl.

Such known mono-valent amino-protecting groups as alkyloxycarbonyl, aralkyloxycarbonyl or aryloxycarbonyl groups may be shown by a formula —CO—$OR_6$ in which $R_6$ is an alkyl group of 1–5 carbon atoms such as methyl, ethyl, t-butyl and t-amyl or a cycloalkyl group of 3–6 carbon atoms such as cyclopentyl and cyclohexyl; an aralkyl group such as phenyl-alkyl containing an alkyl group of 1–4 carbon atoms, for example, benzyl and p-nitrobenzyl; an aryl group such as phenyl, or a heterocyclic group such as furfuryl. Most preferred as amino-protecting groups are t-butoxy and benzyloxy, as these are capable of reacting selectively with the 6'-amino group of the compound (II) and being removed from the acylation products most readily.

For the preparation of such an amino-protected compound of the formula (IV) in which the 6'-amino group alone has been blocked by a known amino-protecting group of the type —CO—$OR_6$, the antibiotic compound of the formula (II) may be reacted with a substantially equimolar proportion of a chloroformate of the formula:

$$Cl-CO-OR_6 \qquad (VII)$$

or a p-nitrophenyl carbonate of the formula:

$$p-NO_2-C_6H_5-O-CO-OR_6 \qquad (VII')$$

or an N-hydroxysuccinimide ester of the formula:

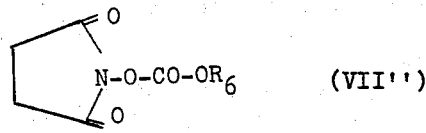

or an azidoformate of the formula:

$$N_3-CO-OR_6 \qquad (VII''')$$

or a 4,6-dimethylpyrimidyl-2-thiol-carbonate of the formula:

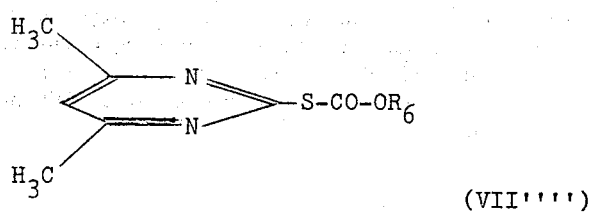

(VII'''')

wherein $R_6$ is as defined above, in a suitable solvent such as water, ethanol, acetone or a mixture thereof under neutral or basic conditions in a manner known in the prior art of synthesis of peptides. The reaction products so obtained usually consist of a mixture of various amino-protected derivatives of the compound (II) comprising the main proportion of derivatives where only the 6'-amino group has been blocked by the group —CO—OR$_6$, as well as minor proportions of derivatives where the 6'-amino group and one or more of the other amino groups have been blocked by the group —CO—OR$_6$, and so on. By subjecting this mixture (said reaction products) to a chromatographic separation using a cation-exchange resin having carboxylic functions, for example, a copolymer of methacrylic acid with divinylbenzene (available under a trade name "Amberlite" IRC 50 or Amberite CG 50, a product of Rohm and Haas, U.S.A., (in the form of the ammonium salt), there may be isolated the starting compound (IV) in which the 6'-amino group alone has been blocked by an amino-protecting group of the type —CO—OR$_6$.

For the preparation of amino-protected compounds of the formula (IV) in which the 6'-amino group alone has been blocked by a known, divalent amino-protecting group of the alkylidene or arylidene type =CHR$_5$, an antibiotic compound of the formula (II) may be alkylidenated or arylidenated by it reacting with a substantially equimolar proportion of an aldehyde of the formula:

 OHC—R$_5$ (VIII)

wherein R$_5$ is as defined above, in a manner known in the production of Schiff's bases. Suitable aldehydes (VIII) for this purpose include acetaldehyde, anisaldehyde, tolualdehyde, p-nitrobenzaldehyde and salicylaldehyde. In this way, there may be obtained the mixed alkylidenation or arylidenation products, which may be subjected to a chromatographic separation using a cation-exchange resin as stated above to isolate the starting compound (IV) in which the 6'-amino group alone has been blocked by amino-protecting group of the type =CHR$_5$.

For instance, 6'-N-t-butoxycarbonyl-kanamycin B or -3',4'-dideoxykanamycin B may be prepared in a high yield by reacting kanamycin B or 3',4'-dideoxykanamycin B in solution in a mixture of pyridine, water and triethylamine with a 1 to 3 molar proportion of t-butoxycarbonyl azide added dropwise thereto under agitation, stirring the admixture at ambient temperature overnight, concentrating the reaction mixture to dryness in vacuo and then purifying the solid residue in a column chromatography with a cation-exchange resin such as Amberlite CG 50 (NH$_4$ form), while recovering the unreacted kanamycin B or 3',4'-dideoxykanamycin B. The compound of the formula (IV) prepared in the above procedures may be employed as the starting compound in the process of this invention without purification.

In acylating the starting compound (IV) with the α-hydroxy-amino acid compound (V) in accordance with the process of this invention, the compound (IV) is reacted with the α-hydroxy-amino acid compound (V) in a manner known for the acylation which is commonly known in the conventional synthesis of amides. Thus, the compound (IV) may be acylated by condensing with the α-hydroxy-amino acid compound (V) in a solution in dimethylformamide, acetone or tetrahydrofuran under ice-cooling and in the presence of a dehydrating agent such as dicyclohexylcarbodiimide. The α-hydroxyamino acid compound (V) employed may either be in the racemic form or in the optically active forms. For example, when an optically active isoserine, such as (L)-isoserine or (D)-isoserine is used as the α-hydroxy-amino acid (V), the final product of the process of this invention is then biologically active similarly to the racemic form. Of course, the α-hydroxy-amino acid compound (V) may also be used in the form of its reactive derivative such as the acid chloride, the mixed acid anhydride, the active esters or the azide derivative thereof. Thus, it is feasible that the α-hydroxy-amino acid compound (V) is at first reacted with N-hydroxysucciimide in the presence of dicyclohexyl-carbodiimide to prepare its active ester of the formula:

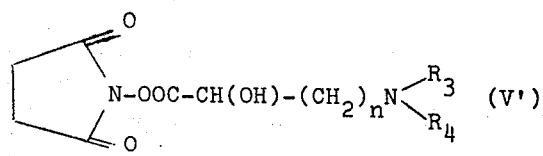 (V')

which is, in turn, reacted with the compound (IV) for the N-acylation of the latter compound. It is preferred that the compound (IV) should be reacted with at least 0.5 molar proportion and preferably 2 to 3 molar proportions of the active ester form of the α-hydroxy-amino acid compound (V') in a reaction medium consisting of water and an organic solvent such as dimethoxyethane. Of the α-hydroxy-amino acid compound (V) or its active ester form (V') which is used as the acylating agent in the process of this invention, it is preferred to use such a form of the α-hydroxy-amino acid compound (V) in which the amino-protecting groups R$_3$ and R$_4$ are of the same nature as that of the amino-protecting groups for the R$_1$ and R$_2$ present in the starting compound (IV) employed.

In the process of this invention, the acylation of the compound (IV) with the α-hydroxy-amino acid compound (V) or (V') gives mixed N-acylated products which are usually composed of a mixture of the desired 1,2'-di-N-acylated product and the undesired mono-N-acylated products as well as the undesired poly-N-acylated products.

The mixed N-acylated products so produced may then be treated so as to remove the remaining amino-protecting groups therefrom, that is to say, to convert the remaining amino-protective groups into hydrogen atoms, respectively.

The removal of the remaining amino-protecting groups from the above-mentioned mixed N-acylated products which are produced by the acylation step of the present process is to convert the amino-protecting groups into hydrogen atoms and may be effected in the following different ways known per se. Thus, when the amino-protecting group is an alkyloxycarbonyl group, such as t-butoxycarbonyl, an cycloalkyloxycarbonyl group, aryloxycarbonyl group, alkylidene or arylidene group, the removal of this kind of amino-protecting group may be effected by subjecting the mixed N-acylated products to a moderate hydrolysis treatment with an acid such as aqueous trifluoroacetic acid, aqueous acetic acid or diluted hydrochloric acid. When the amino-protecting group is an aralkyloxycarbonyl group such as benzyloxycarbonyl, the removal of this sort of the amino-protecting group may be effected by subjecting the mixed N-acylated products to a hydrogenolysis treatment in the presence of a palladium-carbon catalyst or to a treatment with hydrogen bromide in acetic acid. The o-nitrophenoxyacetyl group as the amino-protecting group may be removed by a reductive treatment. When the amino-protecting group is a phthaloyl group, the removal of the phthaloyl group may be achieved by treating the mixed N-acylated products with hydrazine hydrate in ethanol under heating. When the acylation products contain different kinds of the amino-protecting groups, the acylation products may be subjected to simultaneous or successive treatments to remove the different amino-protecting groups therefrom.

After the removal of the amino-protecting group is carried out, the mixed N-acylated products from which the amino-protecting group has been removed are then subjected to a chromatographic separation to remove the unreacted materials and to isolate the desired compound of the formula (I). The removal of the unreacted materials may be effected by column chromatography with silica gel. The isolation of the desired compound of the formula (I) from the mixed N-acylated products may efficiently be achieved by subjecting the mixed N-acylated products to an ion-exchange chromatography using, for example, a cation-exchange resin having carboxylic functions, such as Amberlite IRC 50 or Amberlite CG 50 (a product of Rohm & Haas Co., U.S.A.), a weak cation-exchanger such as CM-Sephadex C-25 (a product of Pharmacia Co., Sweden) or CM-cellulose. The eluate from the chromatographic process is collected in fractions, and the antibacterial activity of these fractions is detected using sensitive and resistant bacteria as the test microorganisms. Through this detection of the antibacterial activity of each fraction, it is easy to locate the active fractions containing the desired compound of the formula (I). A portion is taken out of these active fractions and subjected to a thin layer chromatography with silica gel using, for example, a solvent system of butanol-ethanol-chloroform-17% aqueous ammonia. In this way, it is possible to locate fractions which give a single spot at the specific Rf value of the desired 1,2'-di-N-($\alpha$-hydroxy-aminoacyl)-kanamycin B or -3',4'-dideoxykanamycin B of the formula (I) and which contain solely the desired product (I). Such fractions may be combined together and concentrated to dryness under atmospheric or reduced pressure to recover the desired compound (I).

This invention is not illustrated with reference to the following Examples, to which this invention is not limited in any way.

EXAMPLE 1

Synthesis of 1,2'-di-N-[(S)-4-amino-2-hydroxybutyryl]-kanamycin B.

a. Preparation of 6'-N-tert-butoxycarbonylkanamycin B

Kanamycin B base (4.83 g, 10 millimoles) was dissolved in 100 ml of water, to which was added a solution of 2.40 g (10 millimoles) of tert-butyl-4,6-dimethylpyrimidyl-2-thiol-carbonate in 100 ml of dioxane. The mixture was agitated for 18 hours at ambient temperature to effect the tert-butoxycarbonylation. The reaction mixture was then concentrated to dryness under reduced pressure to give a solid. This solid was dissolved in water and the aqueous solution was passed into a column of 350 ml of a cation-exchange resin consisting essentially of a copolymer of methacrylic acid and divinylbenzene (commercially available as a product of the trade name Amberlite CG 50, ammonium form) to adsorb the butoxycarbonylated products onto the resin. The resin column was washed with 1,400 ml of water and then eluted with 0.2% aqueous ammonia. Those fractions of the eluate which were positive to the ninhydrin reaction and to the Rydon-Smith reaction and also gave a single spot in a high-voltage paper electrophoresis were combined together and concentrated to dryness, affording 2.35 g of a white powder of 6'-N-tert-butoxycarbonylkanamycin B (decomposition point 168°–172°C. Yield 40 %. When the resin column was further eluted with 0.6% aqueous ammonia, the unreacted kanamycin B was recovered in a yield of 1.0 g (21%).

b. Production of 1,2'-di-N-[(S)-4-amino-2-hydroxybutyryl]-kanamycin B.

6'-N-tert-butoxycarbonylkanamycin B (583 mg, 1.0 millimoles) was dissolved in a liquid mixture of 5 ml of water and 5 ml of dimethoxyethane, to which was then added a solution of 800 mg (2.5 millimoles) of N-hydroxysuccinimide ester of (S)-4-tert-butoxycarbonylamino-2-hydroxybutyric acid in 15 ml of dimethoxyethane. The mixture was stirred for 24 hours at ambient temperature to effect the acylation. The reaction mixture was concentrated to dryness under reduced pressure to give a solid comprising the mixed N-acylated products. This solid was taken up into 14 ml of aqueous 90% trifluoroacetic acid, and the resulting solution was allowed to stand at ambient temperature for 40 minutes during which the removal of the tert-butoxycarbonyl groups took place. The reaction solution was then concentrated to dryness under reduced pressure to give 2.19 g of a faintly yellow colored powder. This powder was dissolved in water and the aqueous solution so obtained was then passed into a column of 125 ml of a cation-exchange resin (Amberlite CG 50, ammonium form) to adsorb acylation products onto the resin. The resin column was washed with water (625 ml) and then the resin column was subsequently eluted with 0.5N aqueous ammonia (1,250 ml) and 1N aqueous ammonia (1,250 ml). The eluate was collected in 17 ml fractions, and every fraction was tested according to a usual plate method for its antibacterial activity, using the kanamycin-sensitive strain *Bacillus subtilis* PCI 219 and the kanamycin-resistant strain *Escherichia coli* JR66/W677 as the test microorganisms. Those fractions which showed high antibacterial activity to both of the above strains and which gave a single spot of Rf 0.04 on the thin layer chromatography of silica gel (ART 5721) using methanol-chloroform-28% aqueous ammonia-water (4:1:2:1 by volume) were combined together. The eluate with 1N aqueous ammonia (fractions No. 166–179) was found to contain solely 1,2'-di-N-[(S)-4-amino-2-hydroxybutyryl]-kanamycin B, whereas the eluate with 0.5N aqueous ammonia (fractions No. 88–97) was found to contain solely 1-N-[(S)-4-amino-2-hydroxybutyryl]-kanamycin B which gave a single spot of Rf 0.15 in the above-mentioned thin layer chromatography of silica gel (ART 5721). The fractions No. 166 to 179 combined together were concentrated to dryness under reduced pressure to give 125 mg of a colorless crystalline powder which was identified as 1,2'-di-N-[(S)-4-amino-2-hydroxybutyryl]-kanamycin B. Yield 15%. Decomposition point 177°–180°C. $[\alpha]_D^{26}$ +65° (c 1.25, water).

EXAMPLE 2

Synthesis of 1,2'-di-N-[(S)-4-amino-2-hydroxybutyryl]-3',4'-dideoxykanamycin B a. Preparation of 6'-N-tert-butoxycarbonyl-3',4'-dideoxykanamycin B 3',4'-dideoxykanamycin B base (5 g, 11 millimoles) was dissolved in 555 ml of a mixture of pyridine-water-triethylamine (10:10:1 by volume), to which was then added 1.58 g (11 millimoles) of tert-butoxycarbonyl azide. The admixture was agitated for 18 hours at ambient temperature to effect the tert-butoxycarbonylation. The reaction mixture was then concentrated to dryness under reduced pressure to give a solid. This solid was dissolved in water and the aqueous solution was passed into a column of 300 ml of a cation-exchange resin consisting essentially of a copolymer of methacrylic acid and divinylbenzene (commercially available as a product of the trade name Amberlite CG 50, ammonium form) to adsorb the butoxycarbonylation products onto the resin. The resin column was washed with 1,500 ml of water and then eluted with 0.2% aqueous ammonia. Such fractions of the eluate which were positive to the ninhydrin reaction and to the Rydon-Smith reaction and also gave a single spot in a high-voltage paper electrophoresis were combined together and concentrated to dryness, affording 2.8 g of a white powder of 6'-N-tert-butoxycarbonyl-3',4'-dideoxykanamycin B (decomposition point 136°–140°C). Yield 49%. When the resin column was further eluted with 1% aqueous ammonia, the unreacted 3',4'-dideoxykanamycin B was recovered in a yield of 1.8 g (36%).

b. Production of 1,2'-di-N-[(S)-4-amino-2-hydroxybutyryl]-3',4'-dideoxykanamycin B 6'-N-tert-butoxycarbonyl-3',4'-dideoxykanamycin B (1,107 mg, 2.0 millimoles) was dissolved in a liquid mixture of 20 ml of water and 10 ml of dimethoxyethane, to which was then added 1,544 mg (4.4 millimoles) of N-hydroxysuccinimide ester of (S)-4-benxyloxycarbonylamino-2-hydroxybutyric acid in 20 ml of dimethoxyethane. The admixture was stirred for 19 hours at ambient temperature to effect the acylation. The reaction mixture was concentrated to dryness under reduced pressure to give a solid comprising the mixed N-acylated products.

This solid was taken up into a liquid mixture of 18 ml of trifluoroacetic acid and 2 ml of water, and the resulting solution was allowed to stand at ambient temperature for 30 minutes, during which the removal of the tert-butoxycarbonyl group took place. The reaction solution was then admixed with 16 ml of water and 1 g of 5% palladium-on-carbon and then subjected to the catalytic hydrogenation for 5 hours under atmospheric pressure to effect the removal of the benzyloxycarbonyl amino-protecting group.

The reaction mixture was filtered to remove the catalyst, and the filtrate was concentrated to dryness under reduced pressure to give 3.08 g of a faintly yellow colored powder. This powder was dissolved in water and the aqueous solution so obtained was then passed into a column of 50 ml of a cation-exchange resin (Amberlite CG 50, ammonium form) to adsorb the acylation products onto the resin. The resin column was washed with water (250 ml) and then with 500 ml of 0.5N aqueous ammonia, and the resin column was subsequently eluted with 0.75N aqueous ammonia. The eluate was collected in 10 ml-fractions. Every fraction was tested in the same manner as in Example 1b, and those fractions which showed high antibacterial activity to both the strains Bacillus subtilis PCI 219 and Escherichia coli JR66/W677 and which gave a single spot of Rf 0.09 in the thin layer chromatography of silica gel (ART 5721) using butanol-ethanol-chloroform- 17% aqueous ammonia (4:5:2:5 by volume) were combined together. Fraction Nos. 105 to 137 were found to contain solely the desired 1,2'-di-N-[(S)-4-amino-2-hydroxybutyryl]-3',4'-dideoxykanamycin B, whereas fractions Nos. 75 to 89 were found to contain 1-N-((S)-4-amino-2-hydroxybutyryl)-3',4'-dideoxykanamycin B which gave single spot of Rf 0.17 in the aforesaid thin layer chromatography of silica gel (ART 5721). The fractions Nos. 105 to 137 combined together were concentrated to dryness to give 286 mg of a colorless crystalline powder which was identified as 1,2'-di-N-[(S)-4-amino-2-hydroxybutyryl]-3',4'-dideoxykanamycin B. Yield 18%. Decomposition point 168°–170°C. $[\alpha]_D^{24}$ = +78° (c 1.14, H$_2$O).

EXAMPLE 3

Synthesis of 1,2'-di-N-DL-isoseryl-3',4'-dideoxykanamycin B

6'-N-tert-butoxycarbonyl-3',4'-dideoxykanamycin B (553 mg, 1.0 millimole) was dissolved in a liquid mixture of 5 ml of water and 5 ml of dimethoxyethane, to which was then added a solution of the 755 mg of N-hydroxysuccinimide ester of N-tert-butoxycarbonyl-DL-isoserine in 10 ml of dimethoxyethane. The mixture was stirred at ambient temperature for 16 hours to effect the acylation. The reaction mixture was concentrated to dryness to give a solid comprising the mixed N-acylated products.

This solid was taken up into 14 ml of 90% aqueous trifluoroacetic acid and the solution was allowed to stand at ambient temperature for 40 minutes, during which the removal of the tert-butoxycarbonyl groups took place. The reaction mixture was concentrated to dryness under reduced pressure and the solid residue was taken up into water. The resulting aqueous solution was passed into a column of 20 ml of a cation-exchange resin (Amberlite CG 50, ammonium form) to adsorb the acylation products onto the resin. The resin column was washed with 100 ml of water and then eluted with 0.5N aqueous ammonia. The eluate was collected in 2 ml-fraction. Every fraction was tested in the same manner as in Example 1b, and such fractions which showed high antibacterial activity to both the strains Bacillus subtilis PCI 219 and Escherichia coli JR66/W677 and which gave a single spot of Rf 0.26 in the thin layer chromatography of silica gel (ART 5721) using methanol-chloroform-28% aqueous ammonia-water (4:1:2:1 by volume) were combined together. The fractions Nos. 62 to 64 combined together were concentrated to dryness to give 120 mg of a colorless crystalline powder which was identified as 1,2'-di-N-DL-isoseryl-3',4'-dideoxykanamycin B. Yield 16 %. Decomposition point 175°–178°C. $[\alpha]_D^{27} = +96°$ (c 1.40, water).

EXAMPLE 4

Synthesis of 1,2'-di-N-DL-isoseryl-kanamycin B

6'-N-tert-butoxycarbonyl-kanamycin B (583 mg, 1.0 millimole) was dissolved in a liquid mixture of 5 ml of water and 5 ml of dimethoxyethane, to which was then added a solution of 755 mg of the N-hydroxysuccinimide ester of N-tert-butoxycarbonyl-DL-isoserine in 10 ml of dimethoxyethane. The mixture was stirred at ambient temperature for 16 hours to effect the acylation. The reaction mixture was concentrated to dryness to give a solid comprising the mixed N-acylated products.

This solid was taken up into 14 ml of 90% aqueous trifluoroacetic acid and the solution was allowed to stand at ambient temperature for 40 minutes, during which the removal of the tert-butoxycarbonyl groups took place. The reaction mixture was concentrated to dryness under reduced pressure and the solid residue was taken up into water. The resulting aqueous solution was passed into a column of 30 ml of a cation-exchange resin (Amberlite CG 50 ammonium form) to adsorb the acylation products onto the resin. The resin column was washed with 150 ml of water and then eluted with 0.2N aqueous ammonia (300 ml) and 0.4N aqueous ammonia (300 ml). The eluate was collected in 6 ml-fraction. Every fraction was tested in the same manner as in Example 1b, and such fractions which showed high antibacterial activity to both the strains Bacillus subtilis PCI 219 and Escherichia coli JR66/W677 and which gave a single spot of Rf 0.06 in the thin layer chromatography of silica gel (ART 5721) using butanol-ethanol-chloroform-17% aqueous ammonia (4:5:2:5 by volume) were combined together. The fractions Nos. 82 to 90 combined together were concentrated to dryness to give 120 mg of a colorless crystalline powder which was identified as 1,2'-di-N-DL-isoseryl-kanamycin B. Yield 16%. Decomposition point 180°–185°C. $[\alpha]_D^{27}$ +85° (c 1.0, water).

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope of this invention, can make various changes and modifications of this invention to adapt it to various usage conditions.

What we claim is:

1. A compound selected from the group consisting of 1,2'-di-N-(4-amino-2-hydroxybutyryl)-kanamycin B; 1,2'-di-N-(4-amino-2-hydroxybutyryl)-3',4'-dideoxykanamycin B; 1,2'-di-N-isoserylkanamycin B; 1,2'-di-N-isoseryl-3',4'-dideoxykanamycin B; and the pharmaceutically acceptable acid-addition salts thereof.

2. A compound as claimed in claim 1 which is 1,2'-di-N-(4-amino-2-hydroxybutyryl)-kanamycin B.

3. A compound as claimed in claim 1 which is 1,2'-di-N-(4-amino-2-hydroxybutyryl)-3',4'-dideoxykanamycin B.

4. A compound as claimed in claim 1 which is 1,2'-di-N-isoserylkanamycin B.

5. A compound as claimed in claim 1 which is 1,2'-di-N-isoseryl-3',4'-dideoxykanamycin B.

* * * * *